United States Patent [19]
Feldstein et al.

[11] Patent Number: 5,347,987
[45] Date of Patent: Sep. 20, 1994

[54] SELF-CENTERING ENDOSCOPE SYSTEM

[76] Inventors: David A. Feldstein, 101 Broadway, Creskill, N.J. 07626; Kenneth A. Altman, 38 Homestead Rd., Tenafly, N.J. 07670

[21] Appl. No.: 876,628

[22] Filed: May 4, 1992

Related U.S. Application Data

[63] Continuation-in-part of Ser. No. 682,082, Apr. 8, 1991, abandoned.

[51] Int. Cl.⁵ ............................................. A61B 1/04
[52] U.S. Cl. .......................................... 128/4; 348/65
[58] Field of Search .................... 128/4, 6; 358/98; 73/151; 382/6, 58, 65; 364/413.13

[56] References Cited

U.S. PATENT DOCUMENTS

4,910,590  3/1990  Gillies et al. ..................... 358/98
5,018,509  5/1991  Suzuki et al. ..................... 128/6

Primary Examiner—Jennifer Bahr
Attorney, Agent, or Firm—M. K. Silverman

[57] ABSTRACT

A self-guiding, self-centering endoscope system provides for the advance of a head of the endoscope through the lumen of an internal organ with minimal discomfort to the patient in which use of anesthesia is substantially eliminated. The guiding system is implemented through an algorithm controlled computer processing of 136 coordinate sectors of an electronic mask applied to a video output of the endoscope camera. This output is digitized by a video processing unit and fed into a computer module in which the algorithm compares derived gray scale values of the sectors with a pre-set gray scale parameter to differentiate between levels of varying reflectivity within and upon the walls of the lumen to, thereby, ascertain the best path for the head of the endoscope. Through the use of X- and Y-axis servo-amplifiers and motors, a real time correction of the position of the endoscope head is obtained relative to the center of the lumen.

5 Claims, 7 Drawing Sheets

SELF-CENTERING ENDOSCOPE SYSTEM

REFERENCE TO RELATED APPLICATION

This case is a continuation in part of application Ser. No. 07/682,082, filed Apr. 8, 1991, entitled Self-Centering Endoscope System, now abandoned.

BACKGROUND OF THE INVENTION

In the medical diagnosis of certain internal organs, extensive use is made today of a so-called endoscope by which the internal surface of organs within a body cavity, e.g., the lower intestine, urethra, esophagus, and other such elongated internal organs may be observed through the insertion of the elongated part of the endoscope. In addition to diagnosis, certain treatments can be affected through the use of instruments having an elongated insertible portion.

In the use of such insertible portions of the endoscope, a requirement is that the insertible portion be substantially centered within the body cavity of interest known as the lumen in that, where the insertible element is not centered, the path of advance of the insertible part may be blocked and, in the process, pain or injury may be caused to the patient. Accordingly, a long felt need in the art has been that of a method of advancing the insertible portion of the endoscope in a manner which maintains the inserted portion substantially at the center of the body cavity to be examined.

The present invention makes use of sectors within a defined polar coordinate grid system and a comparison of the light level (known as the gray level) of such sectors relative to certain references. Algorithmic parameters provide a means for continual centering of the insertible end of the endoscope within the lumen.

Numerous mechanical systems, involving servo-driven mechanisms have been known in the art as, for example, is reflected in U.S. Pat. Nos. 4,787,369 (1980) to Allred and U.S. Pat. No. 4,941,454 (1990) to Wood et al. These, and many other electro-mechanical systems, are directed to steerable catheters..Also, endoscopes may be advantageously employed in connection with control information provided by the instant invention in order to achieve real time centering of the head of the endoscope or catheter as it is advanced within the body lumen of interest. The use of computers in monitoring the operation of an endoscope is known in the art, as is reflected in U.S. Pat. No. 4,742,815 (1988) to Ninan et al, entitled Computer Monitoring of Endoscope. Also, the use of gray scale calibrated sectors in controlling the direction of an endoscope is taught in U.S. Pat. No. 4,910,590 (1990) to Gillies et al, entitled Endoscope Insertion Direction Detection Method. The instant invention differs from that of Gillies in that the primary purpose of the instant invention is to control centering of the endoscope, in that state-of-the-art methods of controlling longitudinal and other movements of an endoscope are satisfactory in most applications. Further, the technology of Gillies is far more complex than the method of centering taught herein and, as such, the instant inventive system and method can be made available to a far greater population in need of such diagnostic and treatment equipment because of the economics associated therewith.

A further reference is U.S. Pat. No. 5,018,509 (1991) to Suzuki et al, entitled Endoscope Insertion Controlling Apparatus. Suzuki differs from the instant invention in its use of an algorithm that calls for the use of three generally oval shaped concentric regions in which the relative gray-scale values thereof are compared. Also, Suzuki relies upon a pattern recognition program. Further, Suzuki continually makes use of a system having one-thousand pixels at each edge of the screen. Thereby one million pixels and, in support thereof, a corresponding amount of computer memory is necessary in the operation of the Suzuki system. The present invention, as is more particularly set forth below, makes use of a system of 136 sectors defined in terms of polar coordinates about an origin point, after the initial scan-in of data. The algorithms and related software necessary to implement the inventive system involves comparisons involving only the said 136 sectors, this as compared to the potential need to compare information within one million pixels in the Suzuki system. Further, the Suzuki system does not make use of the entire visual observing field of an endoscope, this being a requirement of the particular algorithm employed by Suzuki.

SUMMARY OF THE INVENTION

The present system relates to a self-guiding, self-centering endoscope system capable of advancing through the lumen of an internal organ with minimal discomfort to the patient in which the use of anesthesia is substantially eliminated. The guiding system is implemented through the computer processing of a polar coordinate mask to the video output from the endoscope camera. The video output is digitized by a video processing unit and fed into a computer module in which an algorithm compares the gray scale values of the sectors derived from the video polar coordinates to determine the necessary X, Y axis adjustments of cross-sectional position and, thereby, the best path for the head of the endoscope. In body cavities, the center of the lumen does not reflect the light source of the endoscope and therefore appears dark, while the walls of the lumen reflect light and therefore appear light by contrast. A gray scale pre-set reference parameter is employed by the algorithm to determine if the head of the endoscope is at the center of the lumen. Thereafter, through the use of X- and Y-axis servo-amplifiers and motors, real time correction of the position of the head of the endoscope relative to the center of the lumen is accomplished.

It is, accordingly, an object of the present invention to provide a self-guiding and self-centering endoscope which will minimize discomfort to the patient substantially eliminating the need for anesthesia, and also reducing the duration of endoscopic procedures.

It is another object of the present invention to provide a self-centering endoscope usable in various treatments as well in diagnostic modalities.

It is a further object of the present invention to provide a control system for a self-guiding endoscope in which the head of the endoscope relative to the lumen of the patient can be constantly monitored in terms of cross-sectional location based upon the reflective properties of the wall of the lumen.

A yet further object is to provide a gray scale imaging system for use with an endoscope such that case of diagnoses and treatment based upon the reflective properties of the tissue of the lumen may be facilitated.

The above and yet other objects and advantages of the present invention will become apparent in the hereinafter set forth Brief Description of the Drawings, Detailed Description of the Invention, and claims appended herewith.

DETAILED DESCRIPTION OF THE INVENTION

The invention relates to a self-guiding, self-centering endoscope which can be employed in either a self-guide mode or in a mode which permits the doctor to manually advance a head 10 of an endoscope 12. As may be noted in the view of FIG. 1, the guiding system is implemented through the computer processing of a video signal 34 from an endoscope camera 13 which is a part of said head 10 of the endoscope 12, having a light source 14.

Figure 2:
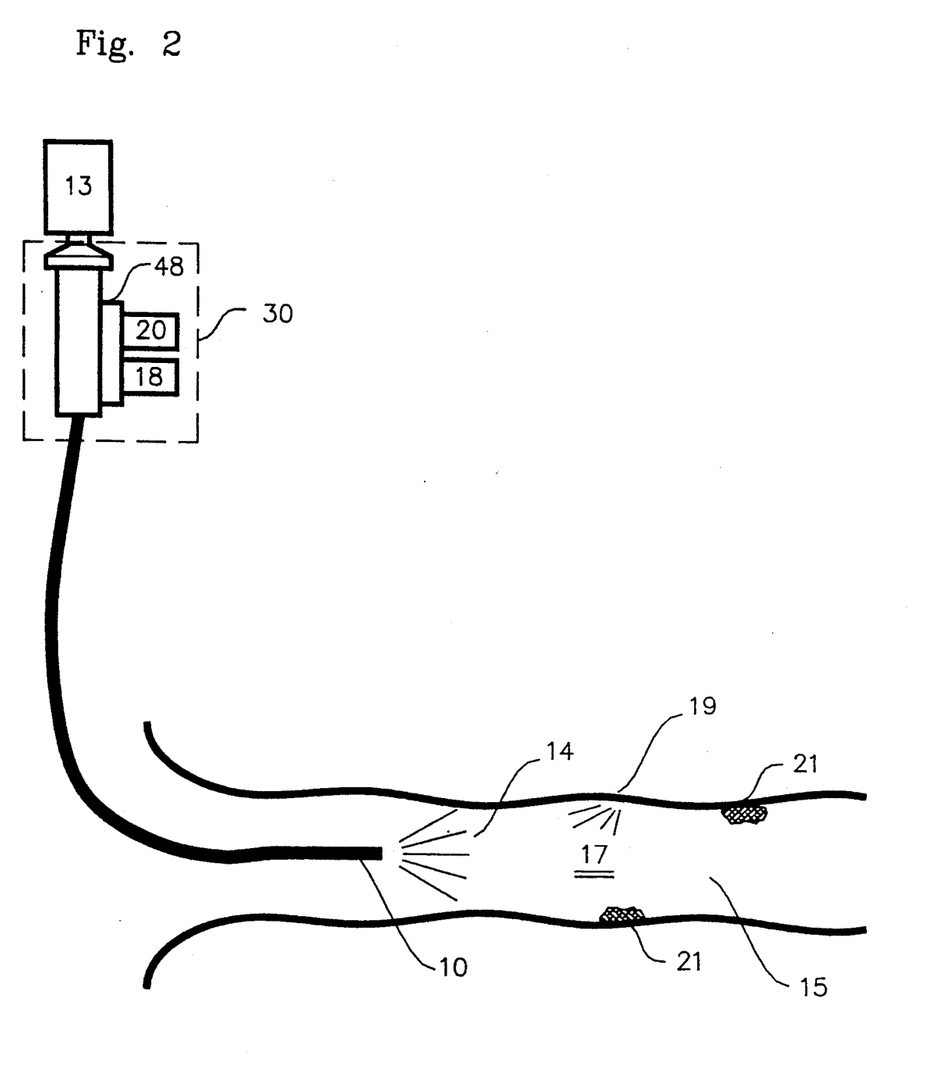
FIG. 2 is a conceptual view of the inside of the lumen of the human body to be examined.

As is more fully described below, a video signal 34 is fed into a computer module 36 and then digitized by a frame grabber 38. A video program having a control algorithm 40 then decides the best path or vector, to the most central point of a lumen 15 of the organ to be examined. This algorithm is based upon a property of the lumen wherein a center 17 thereof does not reflect the light source 14 of the endoscope so that the center 17 appears dark while wall 19 of the lumen reflect the light source and therefore appear light to the endoscope camera. Also shown in FIG. 2 is fecal matter 21 which will also appear dark to endoscope head 10. The algorithm decision (see algorithms described below) is then fed to X, Y and Z servo-amplifiers 16 and then to three servo-motors 18, 20 and 22, which are, respectively, X-axis, Y-axis, and Z-axis servo motors. In the present invention, the Z or longitudinal axis corresponds to the direction of travel, i.e., the longitudinal direction of movement of endoscope head 10 and light source 14, while the X and Y axes refer to the coordinates of the radial cross-section of the lumen.

The inventive configuration allows for a manual control mode employing a digital track-ball 24 as part of a control pod 26. See FIG. 1. The track ball, which is operated while the doctor/technician is observing a video monitor 28, has both two axis (X and Y) and three axis, (X, Y, and Z) capability. Where the control is three axis, the position of the endoscope head will automatically increment a programmed distance in the Z (longitudinal) direction. The track-ball 24 is essentially a joystick which permits the operator of the system to polarly and radially control the position of the head 10, while the button marked "2-axis" on control pod 26 permits manual control of advance forward and backward within the lumen of the endoscope. The buttons to the left of the pod, indicate whether the "automatic" or "control" buttons are to relate to 3-axis or 2-axis automatic or manual control, as the case may be, of the endoscope head.

Figure 1:
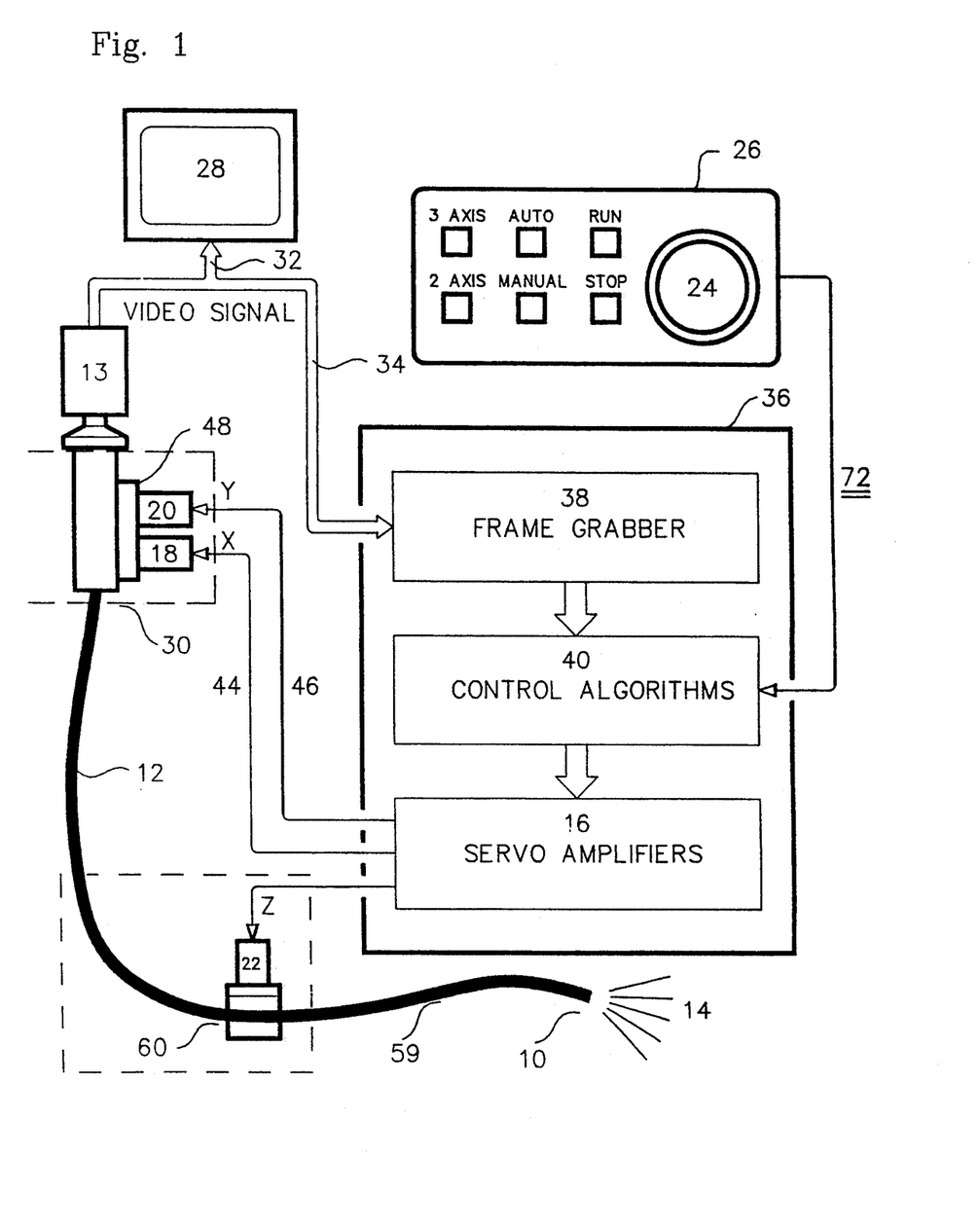
FIG. 1 is a systems block diagram view of the hardware portion of the invention.

With further reference to FIG. 1, it is noted that the path of the video signal 34 in the instant invention commences within the lumen which surrounds endoscope 10 and light source 14. This signal is fed through endoscope cable 12 to a servo control package 30, to video camera 13, and, therefrom, along optical path 32, to video monitor 28. Also, said video signal path 34 is provided leading to computer module 36, and its memory, which includes a video image frame grabber 38, software control algorithm 40, and said servo amplifiers 16. Module 36 may be a PC desktop computer.

As may be further noted, control pod 26 feeds into the control algorithms 40 through electronic line 72. Further, outputs from servo amplifier 16 are provided to X-axis servo motor 18 and Y-axis servo motor 20 by electronic lines 44 and 46 respectively. Interfacing between said servo motors 18 and 20, and said control package 30 is mechanical coupling 48.

Figure 3:
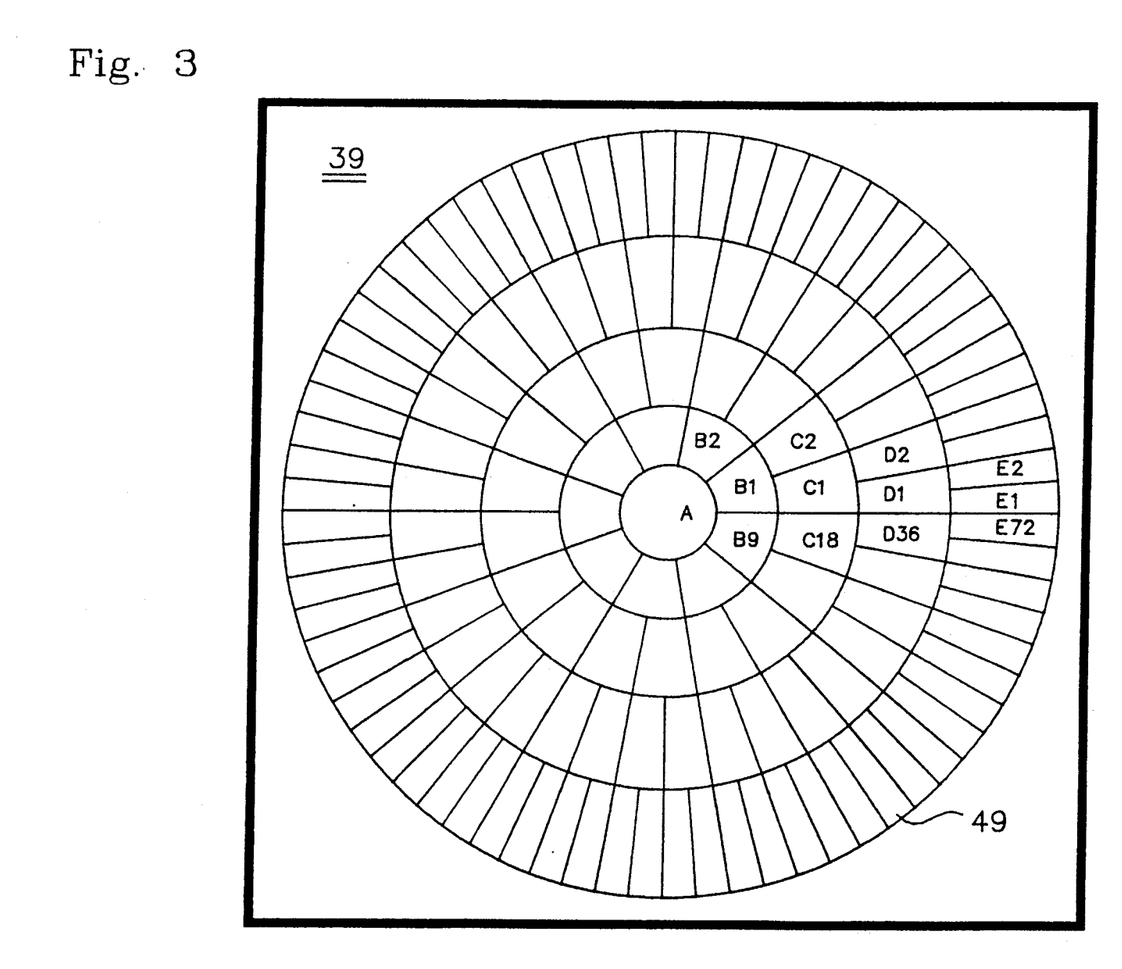
FIG. 3 is a diagrammatic view of a sector memory mask employed with the head of an endoscope employed in the inventive system.

With reference to FIG. 3, there is shown a sector memory mask 49 which, in memory, is applied over each frame 39 "grabbed" by frame grabber 38.

The video signal 34 enters the frame grabber 38 as a black and white analog video signal. The frame grabber then digitizes the video signal into an image of 480×512 pixels, in the case of the standard American RS-170 format (NTSC). An 8 bit analog to digital converter located within the frame grabber 38 is used for this purpose. Each frame of digitized video signal 34 is stored in a frame buffer, which is contained within the frame grabber 38. Frame buffer data is transferred to processor memory as new data is entered into the frame buffer memory thus giving the effect of simultaneous data transfer to processor memory. The digitized signal contains eight bits corresponding to 256 gray value levels and an x, y pixel coordinate location. Frame grabbers such as the commercially available AT-Vista board and Target board from Truevision, can process video signals at 30 flames per second. The frame buffer requires 0.5 megabytes of memory, which is contained within the commercially available frame grabbers. The use of a color video signal is also possible, and would require a 1.5 megabyte frame buffer. The digitized image information is then transferred to a programmable processor on the frame grabber board. The Vista board from Truevision and the Advanced Frame Grabber from Imaging Technologies contain the Texas Instruments TMS 34020 processor. The processor calculates the gray scale values of the sectors defined by sector memory mask 49. It would therefore only be necessary to transfer one gray scale value for each sector into the desktop computer's memory and would significantly decrease the time necessary to process one image. The TMS 34020 processor is capable of performing 20 million floating point operations per second. This high number of operations per second allows real time operation and would enable servomotor correction of the endoscope head 10 at a minimum of ten times per second.

As may be noted, the sector memory mask is based upon a polar coordinate system in which the defined elements, known as sectors, possess a radius selected from radii A, B, C, D and E. Also, the 360° circle defined by the sector memory mask is divided into 72 parts such that the outermost sectors, i.e., the E radius sectors, define a total included angle of 5°. As may be noted, the next inner radius sectors, namely, the D radius sectors define a total included angle of 10°, while the C radius sectors define a total included angle of 20°, with the B radius sectors having total included angle of 40°. Resultantly, there are defined 136 sectors by the sector mask 39. Each of the radii defining the sector ring, separating one group of sectors from the next annular group of sectors, is selected such that the area of each sector, whether in radius A, B, C, D or E, is exactly equal. Accordingly, the radii of the inner rings of the sectors are smaller than are the radii of the outer sector rings. However, the polar angles thereof are greater. The area of each sector in the above described polar coordinate system must be equal so that the potential quanta of light passing through each sector of the sector memory mask will be equal. This equality in potentially received light quanta is necessary as a basis of the later described control algorithms and the principles of reflectivity on which they are based.

Figure 4:
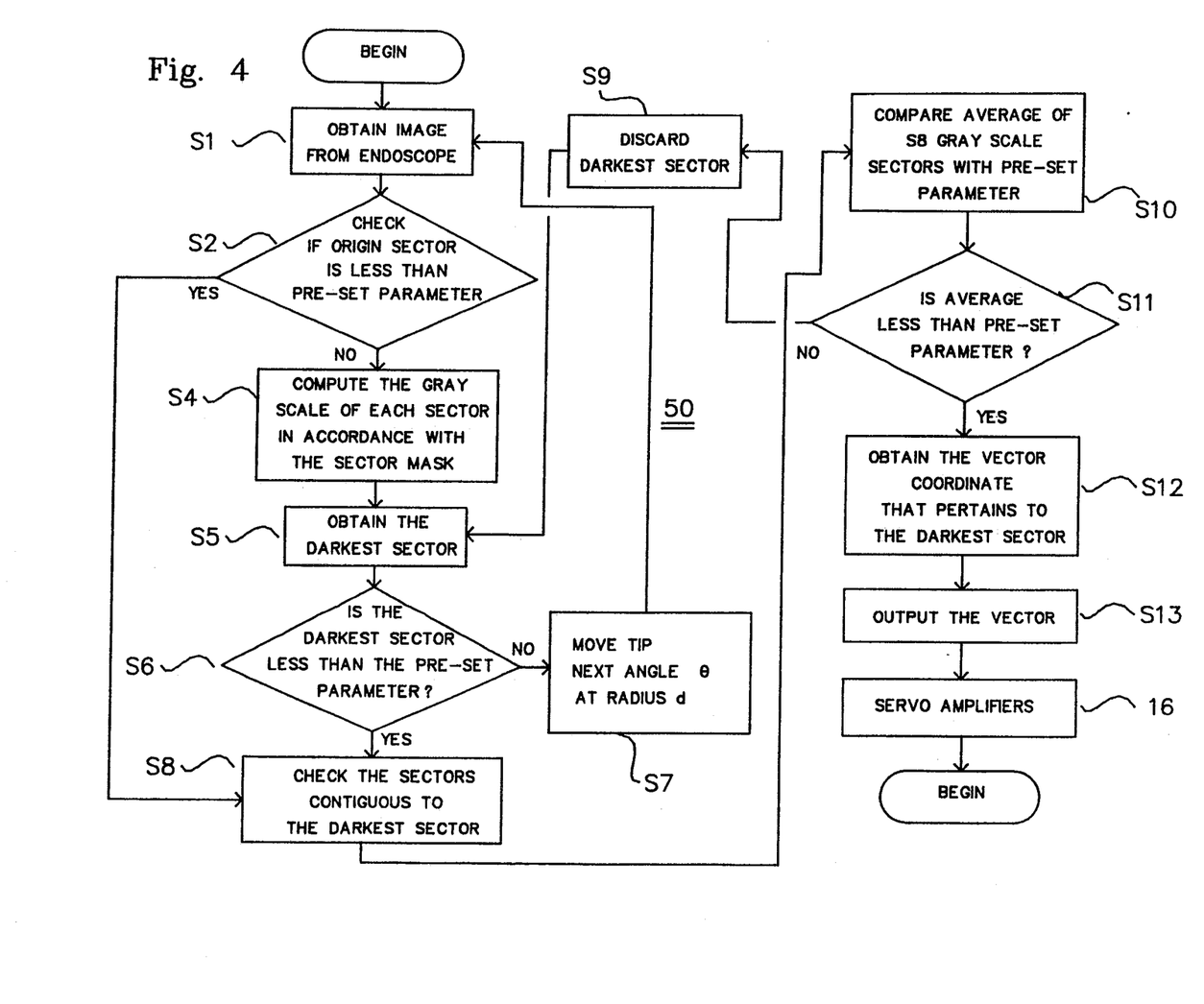
FIG. 4 is a computer software flow diagram showing the first algorithm that may be employed with the inventive system.
Figure 5:
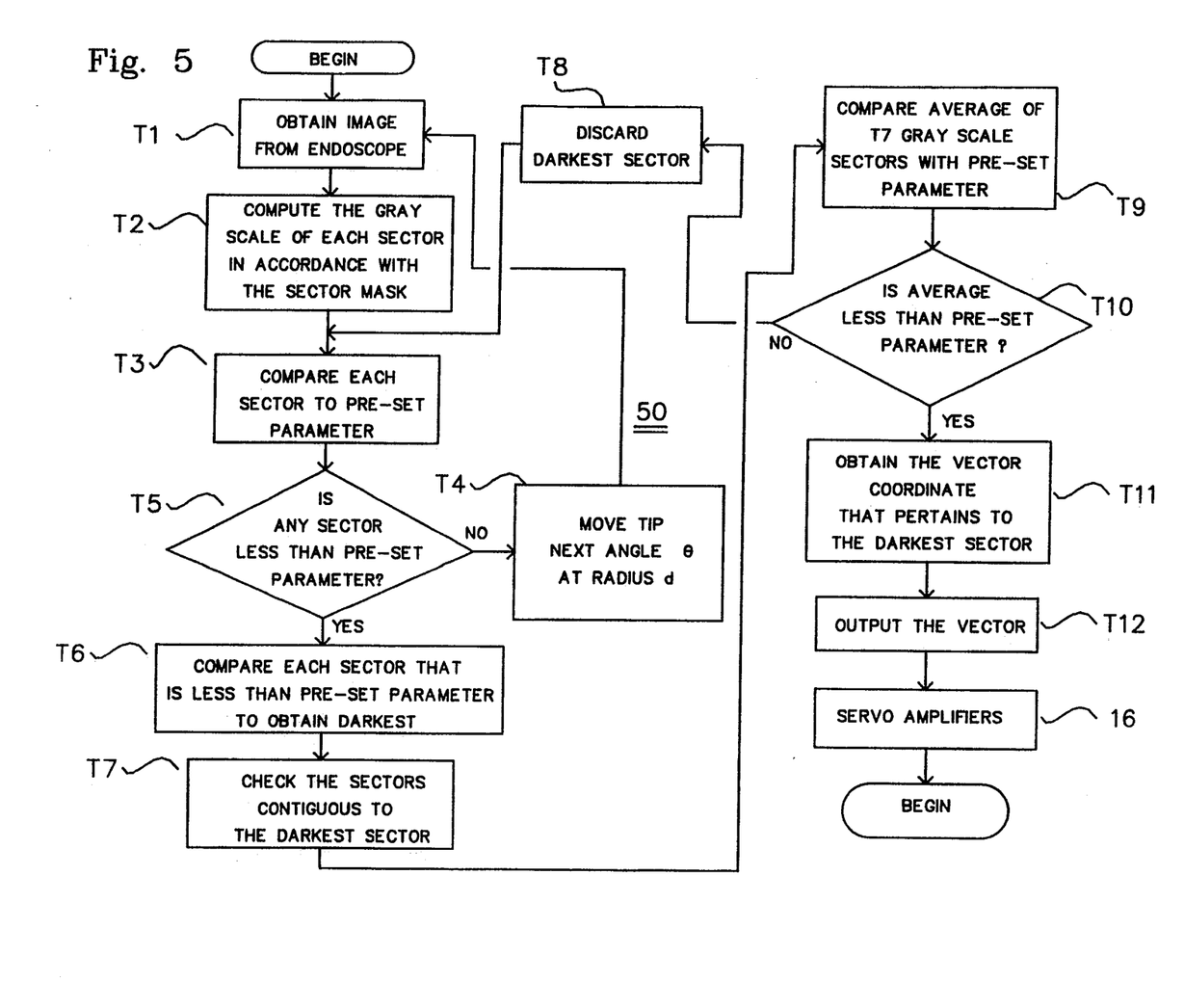
FIG. 5 is a computer software flow diagram showing a second algorithm that may be employed in the inventive system.

Said control algorithm 40 are, more particularly, shown in the flow diagram of FIGS. 4 and 5. It is to be appreciated that the algorithms are responsible for making determinations respective the movement of the endoscope head and, therefore, are responsible for the path the endoscope will take during its advancement.

With further reference to FIG. 4, it is noted in Step S1 that the algorithm first obtains a digitized frame 39 from frame grabber 38 and, thereafter, the sector memory mask 49 is applied to the digitized image obtained from the frame 39. This process will divide the video image into the annular sectors, above described and shown in FIG. 3.

Thereupon, in Step S2 of FIG. 4, the algorithm calculates the gray scale value for the origin sector, that is, sector A of FIG. 3, and then determines whether or not that gray scale value is less than the pre-set gray scale parameter. The pre-said pre-set parameter is a calibrated number obtained for each endoscope make and model, corresponding to a determined number of quanta (photons) of light below which it can be safely surmised that head 10 of the endoscope is pointing substantially toward center 17 of the lumen 15. See FIG. 2. In other words, a higher gray scale value indicates a higher light intensity. Assuming that the darkness of the origin sector checked in Step S2 does meet the pre-set parameter the "yes" path will be followed downwardly to Step S8 in which the memory, that is, the gray scale values of the contiguous sector locations (the B-ring of FIG. 3) that exist in memory will be checked. Thereupon, in Step S10, the average of these contiguous sectors will be compared with the pre-set parameter. If this average is greater than the pre-set parameter Step (S11), there then exists a probability that the origin sector (Sector A of FIG. 3) is actually pointing to fecal matter 21 located upon the wall 19 of the lumen. See FIG. 2. In that event any attempted advance of the endoscope head would be in the direction of the lumen wall 19 and potentially catastrophic. Accordingly, if the answer to the inquiry of the Step 11 is "no", the origin sector is not acceptable as a candidate for the center of the lumen. The origin sector is then discarded as a possibility for the darkest sector and the program then proceeds to Step S5.

Figure 6:
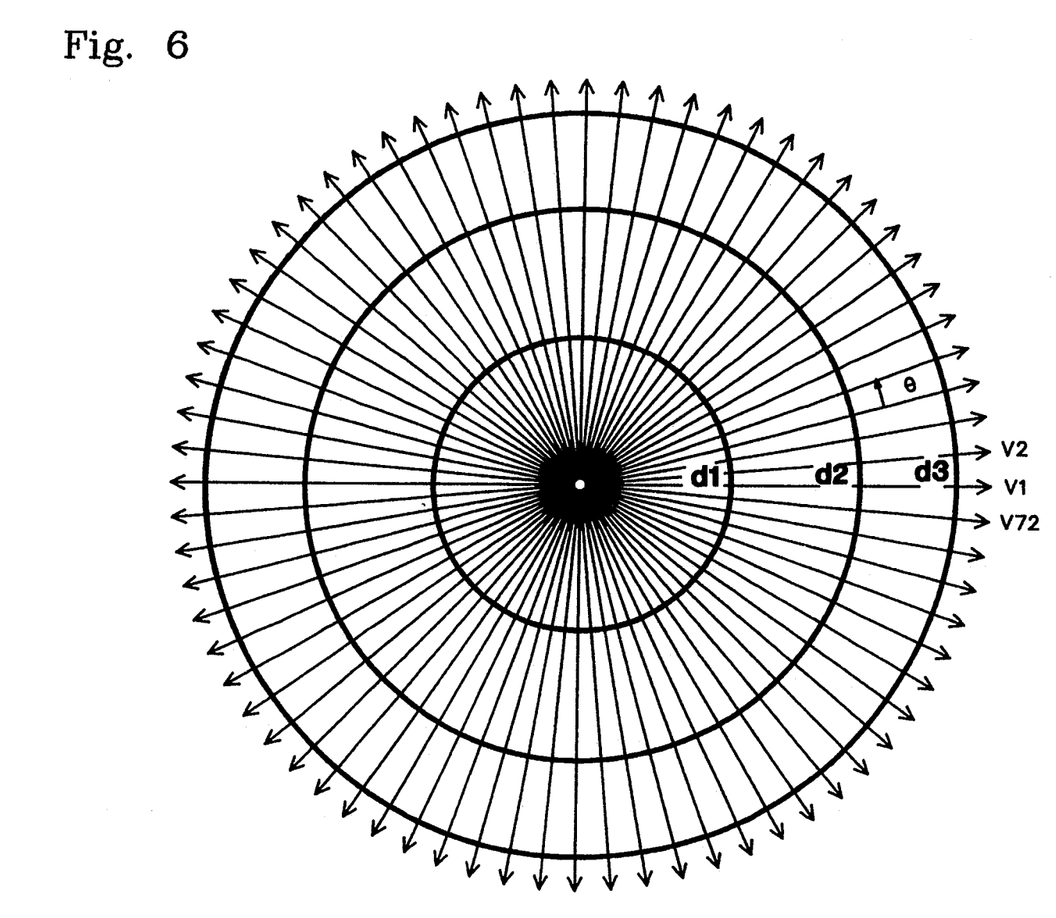
FIG. 6 is a schematic representation of a database structure regarding radial and polar incremental movements of the endoscope head responsive to algorithm processed gray scale information.

If the origin Sector A is greater than the pre-set parameter, the algorithm proceeds to Step S4 in which the algorithm examines the gray scale of each of the sectors in accordance with the sector memory mask 49. See FIG. 4. Thereupon, in Step 5, the darkest sector of the B, C, D, and E rings is obtained. The program then asks the question, in Step S6, of whether or not the darkest sector selected by Step S5 is less than the pre-set parameter, that is, whether the number of photons of light (also expressible in terms of reflectivity) is sufficiently low for purposes of proceeding to Step S8. If the answer is "no", this means that it is possible that no sector within frame 39 is less than the pre-set parameter. If this proves to be the case, the program will advance to Step S7 in which the tip or head of the endoscope is moved an angle at radius d1 as is shown in FIG. 6, noted by path 50 of the program. This routine consists of Steps S1, S2, S4, S5, S6, and S7 and returns to S1, where a new image is obtained. This sequence will be repeated as a search pattern expressed by positions V1 through V72 in FIG. 6 This search pattern is continued until a sector having a gray scale value less than the pre-set parameter is located. If no such sector is found in radius d1 then the search pattern will be repeated in radius d2, and then at a radius D3 until such a sector which is less than the pre-set parameter is located. Accordingly, the routine which includes said path 50 will check potentially 216 positions in the lumen. Therefore if Step S7 is continually repeated a warning signal will be generated and intervention on the part of the examining physician or technician may be necessary to assure that the head of the endoscope is not somehow wedged up against wall 19 of the lumen.

As above noted, the program will proceed to Step S8 if a sector is located in Step S6 which is less than the pre-set parameter. Thereafter, Step S10 will compare the average gray scale value of all sectors contiguous to the candidate darkest sector of Step S5. If this average of contiguous sectors is more than the pre-set parameter (Step S11), this will indicate that the reflectivity of the contiguous sectors is high, i.e., a greater amount of light is reflected by the contiguous sectors than is desired. This result could be caused if fecal matter which is very dark, but small in diameter, was encountered as the darkest sector within Step S5. In such case the program will proceed to Step S9 wherein the current darkest sector is discarded from memory and the program proceeds to Step S5 to obtain the next darkest sector that is in memory.

If the average gray scale value of the contiguous sectors obtained in step S8 is less than the S11 preset parameter, the program will advance to Step S12 in which the computer makes use of a so called look-up table to transpose the selected darkest sector into an XY coordinate. This XY coordinate is outputted as a vector in Step S13 to said servo amplifiers 16 (See FIG. 1) where information is fed, along lines 44 and 46, to servo motors 18 and 20 such that appropriate adjustments of the position of head 10 within the lumen 15 can be made. Thereupon, the system may be either manually or electronically advanced by one increment in the Z (longitudinal) direction whereupon the program is repeated.

In reference to FIG. 5 there is shown a second algorithm which may be employed with the present system. In said figure it is seen that the program begins with Step T1 in which a frame 39 within lumen 15 is obtained. This Step is similar to Step S1 in the program of FIG. 4. Thereupon, Step T2 computes the sector gray scale value of each sector in accordance with the sector mask 49. Thereupon, in Step T3, each of the gray scale levels of each sector are compared to the pre-set parameter whereupon the program asks in Step T5, whether any sector less than the pre-set parameter, that is, is any sector dark enough to possibly be the center of lumen 17. If the answer is no, the program proceeds to Step T4 in which, in the manner described regarding Step S7 of FIG. 4, the endoscope head will be moved in radial increments of d and angular increments the O symbol as are shown in FIG. 6. Accordingly, as above noted with reference to Step S7 in FIG. 4, the reiteration of routine path 50 will constitute potentially 216 reiterations.

If it is determined that some sector within those sectors examined in Step T5 is less than the pre-set parameter, these sectors are then compared with each other (Step T6) to determine which of this set represents the darkest.

Once the darkest sector is thus obtained, the sectors contiguous to this candidate darkest sector are checked in Step T7 in the fashion above described with reference to the Step S8 in the algorithm of FIG. 4. The program then proceeds through Steps T9 through T12 in the same manner above described with respect to Steps S10 through S13 in the algorithm of FIG. 4. It is noted that, in both programs, if the answer to the question of Steps S11 and T10 respectively is "no", the program will proceed along the "no" line into Steps S9 and T8 respectively which determines that the preceding darkest sector should be ignored. The program is permitted to effectively restart itself by returning to Step T3 in the algorithm of FIG. 5 and Step S5 in the algorithm of FIG. 4. If in fact the head of the endoscope has become lodged against fecal matter the program will continually "kickout" of Steps T10 and S11 respectively such that the end of the respective algorithms, T12 and S13 respectively will never be reached. When the program is caught in such an "endless loop" a warning signal will be generated.

As may be appreciated, each sector, regardless of coordinate system, possesses a different amplifying factor that multiplies the motor output Step increments. Once the vector is obtained from the database, the correction vector is outputted to the servo-amplifiers 16 and motors 18 and 20 in Steps S13 and T12 (which is the same function as servo-amplifiers 16). That is, servo-amplifiers 16 output electrical signals to X axis servo 18 and Y axis servo 20. These motors respond to these signals by rotating an X or Y shaft an appropriate number of revolutions.

It is noted that the endoscope head may be programmed to conduct a search pattern comprising a selective polar path followed by a further polar path at a different radius from the mask origin, until the darkest sector on a given frame 39 is located.

Figure 7:
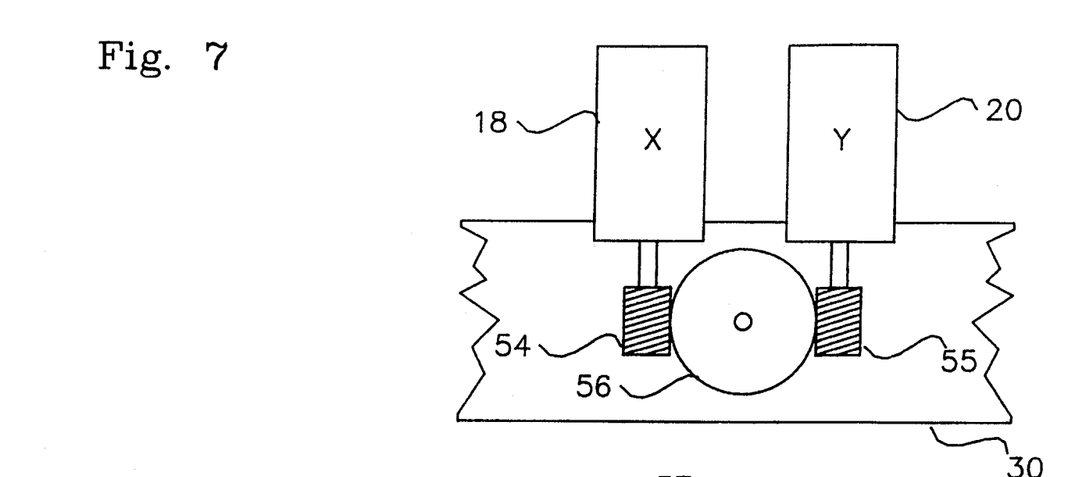
FIG. 7 is a side schematic view of the servo control mechanism found to the left of FIG. 1.
Figure 8:
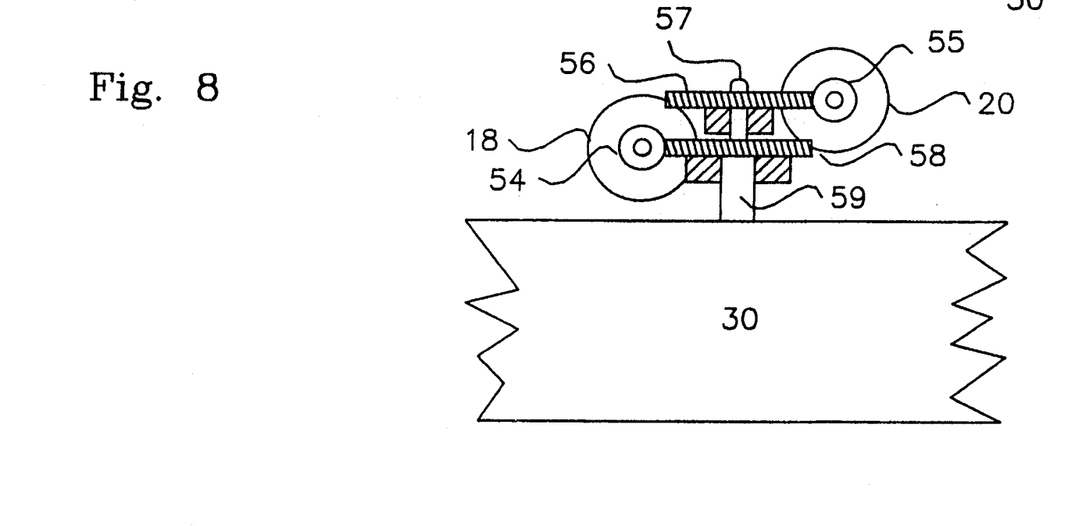
FIG. 8 is a top schematic view of FIG. 7.

The X-axis motor 18's rotation is translated to the outside endoscope shaft 59 via a coupling of a worm drive 54 and a gear 58. See FIGS. 7 and 8. The Y axis motor 20's rotation is translated to the inner endoscope shaft 57 via worm drive 55 and gear 56. In this way, the endoscope head moves in the direction and to the distance computed in the computer algorithm in Step S13 and T12.

Once the endoscope tip is moved, a new picture from the endoscope camera 13 is inputted into the video frame grabber 38 (see FIG. 1) and the endoscope movements are computed and stored. This closes a feedback loop ensuring that the exact position of endoscope tip in relation to the lumen is always a known quantity.

It is noted that the present self-guiding, self-centering endoscope may also be employed in a manual mode which may be easily engaged with a switch on the above described control pod 26. Once manual mode is engaged the endoscope head can be moved using the digital track-ball 24; this produces a digital signal when moved which is inputted into the control computer 36. The exact vector, in terms of X and Y coordinates, is sent to the servo amplifier 16. This output is treated in the same manner as the output of the automatic mode, thereby moving endoscope head the correct direction and distance.

There is optionally provided a Z-axis motor 22 having a mechanical coupling 60 to the outer endoscope shaft 59. See FIG. 1. Said Z-axis motor 22 can be employed with slight software modifications. In this application, the self-guiding endoscope system is totally automatic and will advance until stopped by the operator, releasing the run button of the control pod 26. The system outputs signals at a constant rate to a Z-axis amplifier. This amplifier in turn outputs constant rate of pulses to the Z-axis motor 22 causing a constant endoscope movement through mechanical linkage 60. If the algorithm cannot reach Step S13 or T12, the algorithm 40 will stop outputting the Z axis signals, i.e., will stop any longitudinal movement within the lumen, until the center of the lumen is obtained.

It is to be understood that catheters and the like may be considered endoscopes for purposes of the present invention.

Accordingly, while there has been shown and described a preferred embodiment of the present invention, it is to be appreciated that the invention may be embodied otherwise than as is herein specifically shown and described and that within said embodiment certain changes may be made in the form and arrangement of the parts without departing from the underlying principles or ideas of this invention within the scope of the claims appended herewith.

Having thus described our invention what we claim as new, useful and non-obvious and, accordingly, secure by Letters Patent of the United States is:

1. A system for centering a head of an endoscope within a lumen to be examined, as said head is advanced longitudinally within said lumen, the system comprising:

(a) an endoscope including a head and a light source, said head including a video camera in optical communication with said light source, said endoscope light source and said video camera comprising means for generating a sequence of video frames;

(b) means for acquiring, freezing and digitizing individual frames of said sequence of frames, and storing each digitized frame in a memory location group;

(c) means for establishing a pre-set gray scale parameter corresponding in reflectivity to the center of the lumen to be examined, said pre-set parameter being particularly established for each endoscope make and model;

(d) means, in said memory location group, for applying a co-ordinate sector mask over each stored video frame, each sector of said mask having a digital set of memory addresses equal in number to every other stored sector sets.

(e) means for assigning a gray scale value for each of said sectors within said sector mask, in which an average value of the gray scale values of the digital set of each sector in memory is taken;

(f) means for establishing computer memory location for each assigned gray scale sector value;

(g) means for obtaining the darkest sector in said memory locations;

(h) means for determining if said gray scale value of said darkest sector is less than said pre-set parameter;

(i) means for determining if an average gray scale value of sectors contiguous to said darkest sector is less than said pre-set parameter;

(j) means for utilizing further search patterns if said darkest sector is greater than the pre-set parameter, said means comprising means for angularly advancing a tip of said head of said endoscope in discreet circular search patterns of successively increasing radii until a sector is located which is less than the pre-set parameter;

(k) means for calculating a vector between said located sector and the origin of the sector mask; and (l) feedback means for servo-mechanically re-positioning said endoscope head in accordance with said calculated vector.

2. The system as recited in claim 1, said system further comprising:

(k) means for discarding said darkest sector if said gray scale average value of said contiguous sectors is greater than said pre-set parameter; and (l) means for obtaining a new darkest sector after a current one is discarded.

3. The system as recited in claim 1, further comprising: means for computing the gray scale value of the origin sector of said sector mask and comparing the same with the pre-set parameter prior to computing the gray scale value of other sectors of the sector mask.

4. A system for centering a head of an endoscope within a lumen to be examined, as said head is advanced longitudinally within said lumen, the system comprising:

(a) an endoscope including a head and a light source, said head including a video camera in optical communication with said light source, said endoscope light source and said video camera comprising means for generating a sequence of video frames;

(b) means for acquiring, freezing and digitizing individual frames of said sequence of frames, and storing each digitized frame in a memory location group;

(c) means for establishing a pre-set gray scale parameter corresponding in reflectivity to the center of the lumen to be examined, said pre-set parameter being particularly established for each endoscope make and model;

(d) means, in said memory location group, for applying a coordinate sector mask over each stored video frame, each sector of said mask having a digital set of memory addresses equal in number to every other stored sector sets;

(e) means for assigning a gray scale value for each of said sectors within said sector mask, in which an average value of the gray scale values of said digital set of each sector in memory is taken;

(f) means for establishing computer memory location for each assigned gray scale sector value;

(g) means for comparing the gray scale values of each sector of said sector mask to said pre-set gray scale parameter;

(h) means for comparing the gray scale levels of all sectors that are less than the pre-set parameter to obtain the darkest sector thereof, if any of such sectors are less than said pre-set parameter;

(i) means for utilizing further search patterns if none of said sectors is less than the pre-set parameter, said means comprising means for angularly advancing a tip of said head of said endoscope in discreet circular search patterns of successively increasing radii until a sector is located which is less than the pre-set parameter;

(j) means for determining if an average gray scale value of sectors contiguous to said darkest sector is less than said pre-set parameter;

(k) means for calculating a vector between said located sector and the origin of the sector mask; and (l) feedback means for servo-mechanically re-positioning said endoscope head in accordance with said calculated vector.

5. The system as recited in claim 4, said system further comprising:

(m) means for discarding said darkest sector if said gray scale average value of contiguous sectors is greater than the pre-set parameter; and (n) means for obtaining a new darkest sector after the current darkest sector is discarded.

* * * * *